United States Patent [19]

Rice

[11] Patent Number: 4,613,668

[45] Date of Patent: Sep. 23, 1986

[54] SHORT TOTAL SYNTHESIS OR MORPHINAN COMPOUNDS WHICH USES CYCLIZATION OF A CYCLOALKYLCARBONYL COMPOUND SELECTED FROM CYCLOPROPYLCARBONYL AND CYCLOBUTYLCARBONYL

[75] Inventor: Kenner C. Rice, Rockville, Md.

[73] Assignee: The United States of America as represented by the Department of Health and Human Services, Washington, D.C.

[21] Appl. No.: 564,515

[22] Filed: Dec. 22, 1983

[51] Int. Cl.[4] ............................................. C07D 489/02
[52] U.S. Cl. ..................................... 546/44; 546/15; 546/45; 546/74; 546/146; 546/149
[58] Field of Search ................... 546/44, 45, 146, 149, 546/74, 46

[56] References Cited

U.S. PATENT DOCUMENTS

| | | | |
|---|---|---|---|
| 3,299,072 | 1/1967 | Bartels-Keith | 546/44 |
| 3,322,771 | 5/1967 | Bartels-Keith | 546/44 |
| 4,003,903 | 1/1977 | Schwartz | 546/146 X |
| 4,058,531 | 11/1977 | Monkovic et al. | 546/74 |
| 4,115,389 | 9/1978 | Monkovic | 546/74 X |
| 4,139,534 | 2/1979 | Lim et al. | 546/74 |

FOREIGN PATENT DOCUMENTS

| | | | |
|---|---|---|---|
| WO82/144 | 1/1982 | PCT Int'l Appl. | 546/74 |
| WO82/4049 | 11/1982 | PCT Int'l Appl. | 546/74 |

OTHER PUBLICATIONS

Bartels-Keith, J. Chem. Soc. (C), 1966, pp. 617–624, (1966).
Monkovic, et al., J. Am. Chem. Soc., vol. 100, No. 14, pp. 4609–4610, (Jul. 5, 1978).
Rice, J. Org. Chem., vol. 45, No. 15, pp. 3135–3137, (Jul. 18, 1980).
Weller et al., J. Med. Chem, vol. 19, No. 10, pp. 1171–1175, (10/76).
Wiberg and Kass, J. Am. Chem. Soc., 107:988–95, 1985, refs. 1–30.
Wiberg et al., J. Am. Chem. Soc., 107:1003–07, 1985.
Houben-Weyle, vol. 4, Part 3, p. 651, "Methods of Organic Chemistry," Springer-Verlag Press, 1971.
E. H. Rodd, Chemistry of Carbon Compounds, vol. II-A, p. 27.
Giacomini, et al., J. Org. Chem., 45:519–22, 1980.
Olah, et al., Synthesis, 1973, pp. 661–664.
Olah, et al., Science, vol. 206, pp. 13–20, 1979.
Howells and McCown, Chemical Reviews, 1977, pp. 69–92.
Schultz, J. Org. Chem., 36(3):383–386, 1971.
M. C. Brande, et al., (Eds), Advances in Biochemical Pharmacology, vol. 8, 1974, p. 46.

*Primary Examiner*—Donald G. Daus
*Assistant Examiner*—Diana G. Rivers
*Attorney, Agent, or Firm*—John S. Roberts, Jr.

[57] ABSTRACT

There is disclosed herewith a method of producing morphinan compounds by total synthesis which incorporates utilization of N-cycloalkylcarbonyl compounds, which show certain advantages over the prior art which has been previously expressed in U.S. Pat. No. 4,368,326.

1 Claim, No Drawings

SHORT TOTAL SYNTHESIS OR MORPHINAN COMPOUNDS WHICH USES CYCLIZATION OF A CYCLOALKYLCARBONYL COMPOUND SELECTED FROM CYCLOPROPYLCARBONYL AND CYCLOBUTYLCARBONYL

There is disclosed herewith a method of producing morphinan compounds by total synthesis which incorporates utilization of cycloalkylcarbonyl compounds, which show certain advantages over the prior art which has been previously expressed in U.S. Pat. No. 4,368,326.

MATERIAL INFORMATION DISCLOSURE

In the standard manufacturing methods of preparing narcotic antagonists and agonist-antagonist drugs, such as Naltrexone, Nalbuphine, Buprenorphine, and Nalmefene, the starting material utilized is natural thebaine, which has an N-methyl substituent present. The thebaine is in process through a number of steps depending upon which compound is to be prepared and at some stage involves removal of the N-methyl substituent and replacement of the N-methyl substituent with an N-cycloalkylmethyl substituent, which confers the desired pharmacological profiles on the above-mentioned drugs.

In U.S. Pat. Nos. 4,368,326 and 4,410,700 Rice, although thebaine with the natural opium absolute configuration can be prepared by total synthesis from intermediates described in these patents, this would not differ from the standard production of thebaine-derived materials which involves replacement of the methyl by cycloalkyl methyl substituents.

U.S. Pat. Nos. 3,322,771 and 3,299,072 Bartels-Keith describe transformation of certain opium derivatives obtained by degradation natural codeine, morphine or thebaine to intermediates useful for preparation of pharmacologically important drugs. These disclosures of course rely completely on opium as raw material.

In the present process, which does not involve the intermediary of any natural opium derivative, N-methylated or N-normorphinan intermediates, the production of intermediates valuable for synthesis of the above-mentioned drugs and others is addressed by total synthesis from m-methoxyphenethylamine. This process takes the opposite direction from utilization of natural materials, thus it obviates the need for opium and its extractives as raw materials for production of Naltrexone, Buprenorphine, Nalbuphine and Nalmefene.

In the present process, which is a total synthesis of cycloalkylmethyl northebaine derivatives as intermediates to Naltrexone, Buprenorphine, Nalbuphine, Nalmefene, and chemically and pharmacologically similar compounds, the cycloalkyl substituent is introduced at an early stage in the synthesis prior to formation of the morphinan carbon-nitrogen skeleton. In order for the directed Grewe cyclization to occur as described in U.S. Pat. No. 4,368,326, the nitrogen must be protected, and in that patent an N-formyl substituent was used for protection of the nitrogen.

In the present process, a cycloalkylcarbonyl substituent is used first as a protecting group for nitrogen in the Grewe cyclization and then this substituent is carried through the sequence and later serves as precursor for the cycloalkylmethyl substituent present in the northebaine derivatives. This obviates the need for natural thebaine, the use of which entails the replacement of methyl by other substituents for synthesis of antagonist and agonistantagonist drugs. In essence, the cycloalkylcarbonyl substituent on nitrogen serves a double purpose protecting an esoteric precursor and for the cycloalkylmethyl substituents after the morphinan carbon-nitrogen skeleton is formed. See Chart 1.

If the compounds such as Naltrexone (ENDO) Buprenorphine (Reckitt and Coleman), Nalbuphine (ENDO), and Nalmefene (Key) are prepared using intermediates described in the Rice U.S. Pat. No. 4,368,326, N-formyl or N-methyl intermediates are obligatory intermediates and these N-substituents must be replaced with N-cycloalkyl methyl. In the present process, removal of N-substituents and replacement with others is unnecessary and this results in a net saving of a substantial number of steps in the overall total synthesis. This is a process designed to eliminate the need for opium and thus differs from the standard manufacturing process which requires the natural opium derivative thebaine, which is usually in short supply in this country. In the original U.S. Pat. No. 4,368,326, compound 7 is obtained which is a racemic 1-benzyltetraisoquinoline. This compound is easily resolved as described in the Rice U.S. Pat. No. 4,410,700 through using the tartrate salts to provide either the (+)- or the (−)-nor-compound, the (+)- or (−)-isomer of 7. The (+)-isomer of 7, also available by chiral reduction of 6, when carried through the total synthesis, affords the opiates with the natural configuration, such as those derived from natural thebaine, whereas the (−)-isomer of 7, equally available by optical resolution or chiral reduction of 6, will afford by corresponding sequence of reactions access to the unnatural opiate series, thus providing compounds such as (+)-Naltrexone, (+)-Buprenorphine, (+)-Nalbuphine and (+)-Nalmefene. These compounds are of potential value as antitussive agents and, since these compounds are not available by synthesis from opium, the present total synthesis provides access to these unnatural (+)-isomers in any desired quantity and may provide new antitussives or drugs with unidentified pharmacological properties as yet.

The (+)-enantiomers of codeine and a number of other (+)-opiates are known to be potent antitussive compounds, and it may be that the as-yet unsynthesized (+)-opiate enantiomers will prove to provide additional antitussive drugs. See Takagi et al., *Yakugaku Zasshi*, 80:1506 (1960) and T. T. Chan and L. S. Harris, *J. Pharm. Exp. Ther.*, 215:668 (1980).

In general, the basic difference between the present process and the work of Bartels-Keith is that in the present process the thrust is production of opium derivatives by total synthesis without using any opium-derived materials, whereas in Bartels-Keith's work, which does not address total synthesis, his intermediates are prepared by degradation of natural opium alkaloids such as thebaine and codeine. Furthermore, in the present invention the majority of the intermediates are novel compounds which were not described by Bartels-Keith. These are the compounds leading to the morphinans, and those morphinans which have bromine in the aromatic ring, which was required by the general method for directed Grewe cyclization in order to direct the Grewe cyclization to provide the oxygenation pattern present in the opium alkaloids.

Chart 1 below shows the total synthesis of the morphinan compounds according to the present invention.

Chart 2 below is an illustration of certain modern compounds embodying the cycloalkylmethyl ring structure.

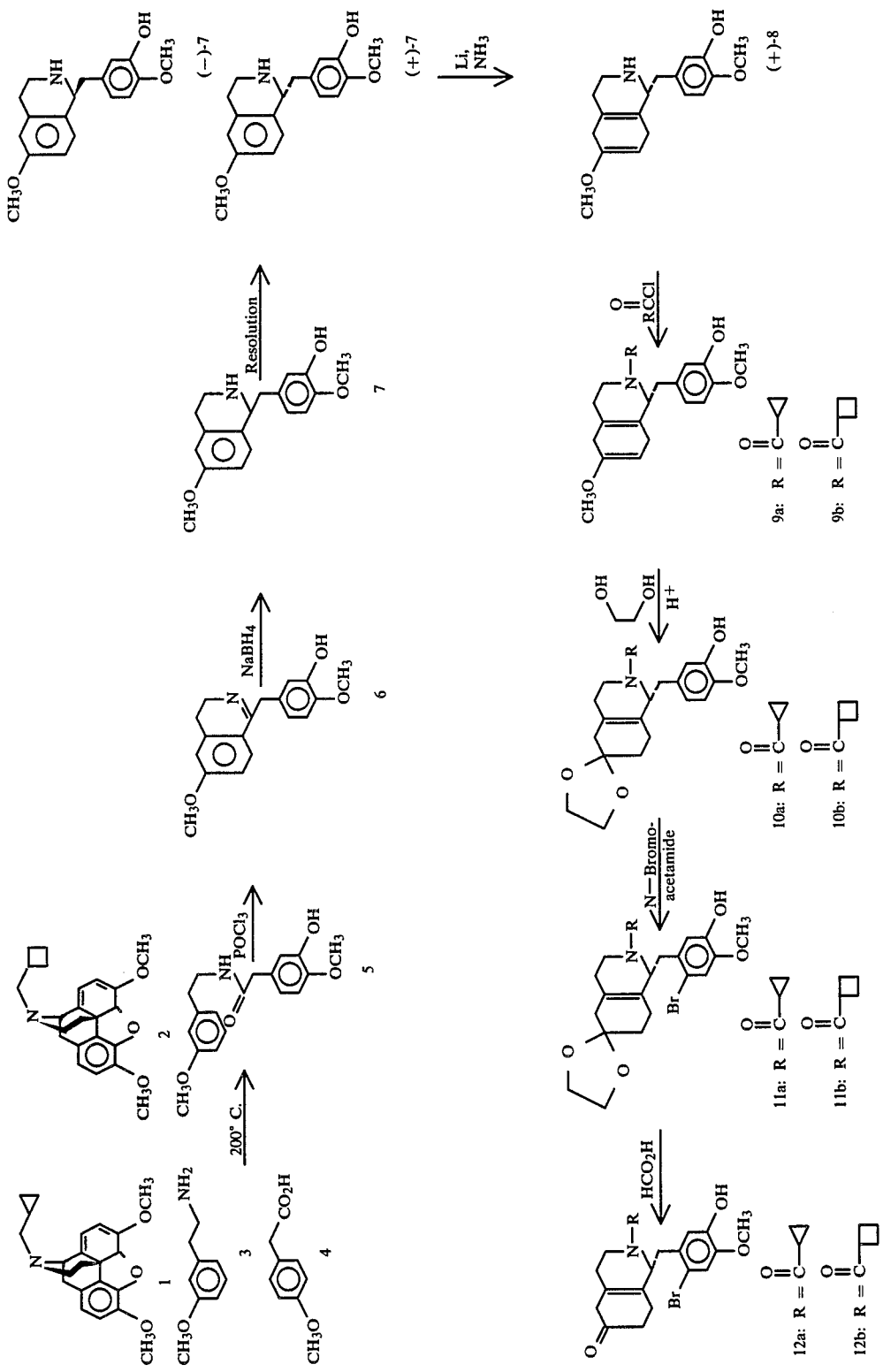
CHART 1

-continued
CHART 1
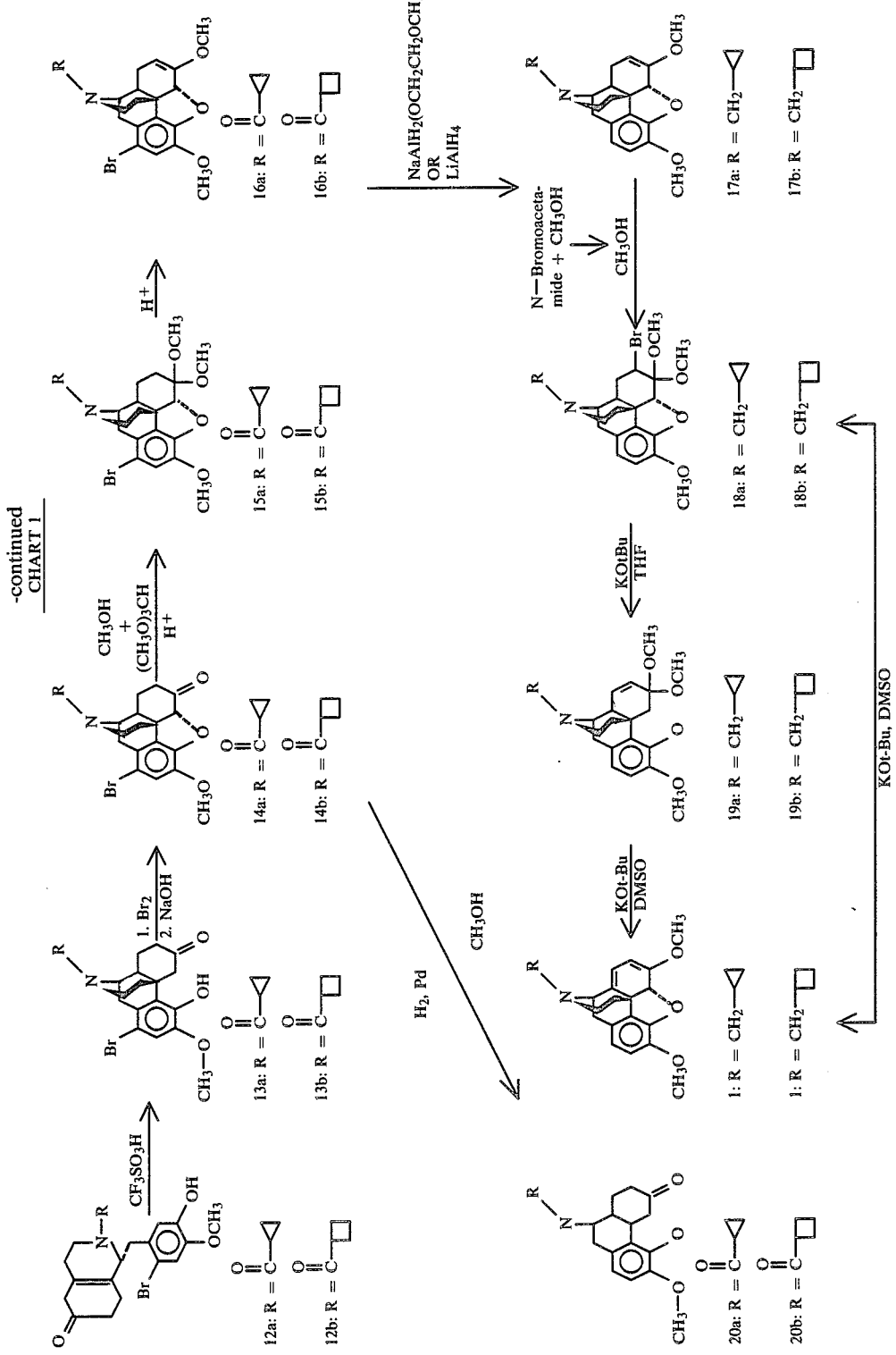

CHART 2

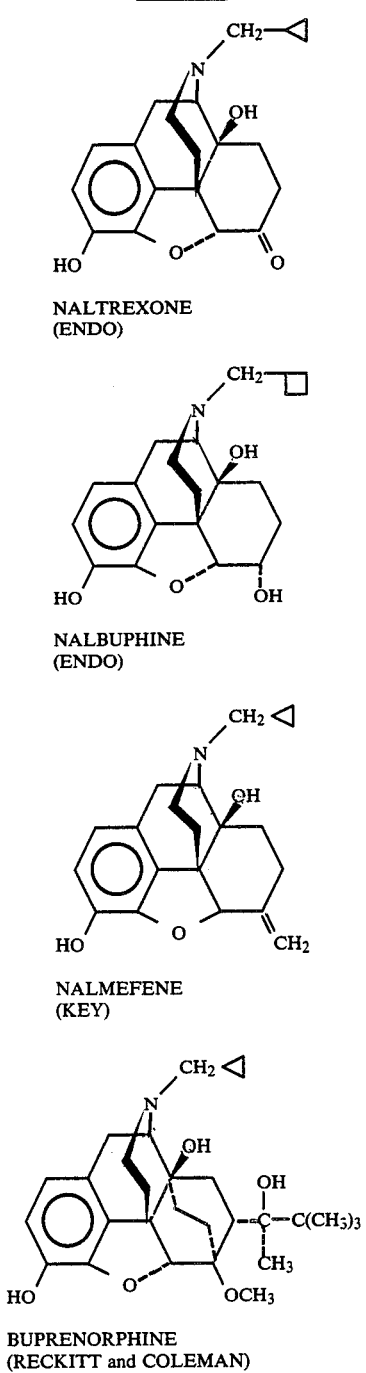

NALTREXONE
(ENDO)

NALBUPHINE
(ENDO)

NALMEFENE
(KEY)

BUPRENORPHINE
(RECKITT and COLEMAN)

In the present process which is the same as that shown in U.S. Pat. No. 4,368,326 to compound 7, optical resolution of compound 7, as described in U.S. Pat. No. 4,410,700, provides (+)-7 and (−)-7 of demonstrated optical purity. (+)-7, obtained by optical resolution, or asymmetric reduction of 6, eventually affords access to the morphinans with the natural opium configuration. Compound (+)-7 is reduced to the Birch base (+)-8. Treatment of (+)-8 with cyclopropylcarbonyl chloride or cyclobutylcarbonyl chloride in a two-phase system consisting of a hydrocarbon or a preferred halogenated hydrocarbon solvent and aqueous carbonate or bicarbonate affords the corresponding optical isomers of compound 9a and 9b where R is equal to the cyclopropylcarbonyl and cyclobutylcarbonyl. Treatment of both of these compounds analogous to U.S. Pat. No. 4,368,326 with ethylene glycol and an acid provides the corresponding cycloalkylcarbonyl derivatives 10a and 10b. In each of these compounds, treatment with N-bromoacetamide as described affords the corresponding bromo derivatives 11a and 11b. Deketalization of the two cycloalkyl carbonyl derivatives of 11a and 11b with formic acid as described affords the corresponding beta,gamma unsaturated ketones 12a and 12b, where R is equal to either cyclopropylcarbonyl and cyclobutylcarbonyl as shown. Treating each of these compounds with trifluoromethanesulfonic acid, or other super acid, affords the morphinone derivatives 13a and 13b corresponding to compound 17 in U.S. Pat. No. 4,368,326. The two derivatives produced by the cyclization are the N-cyclobutylcarbonyl and cyclopropylcarbonyl derivatives. As far as novel compounds go to this point, all compounds beginning with the number 9 and including 13a and b are novel compounds.

The novelty of the present invention is heightened by the fact that in ordinary prior art parlance the instability to strong acid of the cyclopropane ring and to a lesser extent the cyclobutane ring is well known. In the present invention, disclosure is made of the highly surprising finding that the cyclopropyl and cyclobutyl of 12a and 12b are stable to treatment with trifluoromethanesulfonic acid or other super acid required for formation of morphinans 13a and 13b, Fieser and Fieser, *Advanced Organic Chemistry*, Reinhold, 1961, p 534–535. This fact is an important one in the development of the present invention. The reasons for this observed stability of these three- and four-membered cycloalkyl rings under the conditions utilized in the Grewe cyclization are not known at this time.

In the present work the following compounds are believed to be new compounds using the numbering system in Chart 1, starting with compound 9a and 9b, proceeding through 10a, 10b, 11a, 11b, 12a, 12b, 13a, 13b, 14a, 14b, 15a, 15b, 16a, and 16b.

SPECIFIC DESCRIPTION OF THE METHOD

A method which comprises heating a mixture of an amine compound of the formula 3, chart 1, and pure acid compound 4 at 200° C. for about two hours under argon or other inert gas to obtain an amide compound 5. Contacting compound 5 with phosphorus oxychloride to produce the 1,2-dehydro derivative compound 6, which need not be isolated, neutralizing the 1,2-dehydro derivative compound 6 with aqueous ammonia and reducing with sodium borohydride or sodium cyanoborohydride to give the racemic tetrahydroisoquinoline 7. Optical resolution of tetrahydroisoquinoline 7 with the tartaric acids or nitrotartranilic acids gives the (+)-isomer of 7, which can also be obtained by reduction of 6 with chiral hydride reagents. Treating compound (+)-7 with lithium, liquid ammonia or lower alkyl amine and a mixture of tetrahydrofuran and t-butanol containing potassium tertiary butoxide gives the Birch base compound (+)-8. Treating compound (+)-8 with cyclopropylcarbonyl chloride in a two-phase mixture of aqueous carbonate or bicarbonate and a hydrocarbon or halogenated hydrocarbon solvent such as chloroform or methylene chloride to give compound 9a, where R is equal to cyclopropylcarbonyl. Analogously treating compound (+)-8 with cyclobutylcarbonyl chloride in the same two-phase system gives the corresponding compound 9b.

Treating 9a and 9b with ethylene glycol and $CH_3SO_3H$ or other acid in tetrahydrofuran gives compounds 10a and 10b, which need not be isolated, but can be directly brominated with N-bromoacetamide to give the corresponding bromoethylene ketals 11a and 11b, shown in Chart 1. Deketalization of these compounds by a brief treatment with 88% formic acid gives compounds 12a and 12b, respectively. These compounds are the beta,gamma unsaturated ketones and the direct precursors of the morphinone compounds 13a and 13b. Treating compounds 12a and 12b with trifluoromethanesulfonic acid, or other super acid, gives compounds 13a and 13b, which are N-cycloalkylcarbonyl bromonordihydrothebainone derivatives.

Treating compounds 13a and 13b with about an equal molar amount of bromine in chloroform or acetic acid followed by treating with excess sodium hydroxide gives compounds 14a, 14b, in which the oxide bridge is closed. These compounds are the cycloalkylcarbonyl bromonordihydrocodeinone derivatives.

Treating compounds 14a and 14b with trimethylorthoformate and methanol and a sulfonic acid such as p-toluenesulfonic acid or preferably 5-sulfosalicylic acid gives compounds 15a and 15b, which need not be isolated. Distillation of the organic solvent and the methanol formed converts the compounds 15a and 15b generated in situ to the corresponding enol ethers 16a and 16b. Reduction of the bromo amides 16a and 16b with lithium aluminum hydride or preferably with a sodium aluminum hydride reagent shown gives the corresponding amine compounds 17a and 17b, where R equals cyclopropylmethyl and cyclobutylmethyl, respectively.

In this reduction two reactions are accomplished at once—the displacement by hydride ion of the bromine atom from the aromatic ring and reduction of the amide function.

Treating compounds 17a and 17b, which are 8,14-dihydro derivatives of cycloalkylmethylnorthebaines with N-bromoacetamide in methanol gives compounds 18a and 18b, which are 7-bromo derivatives of the cycloalkylmethyl nordihydrocodeinone dimethylacetals. These compounds 18a and 18b can be converted to the corresponding cycloalkylmethylnorcodeinone dimethylketal compounds 19a and 19b by treatment with potassium tertiary butoxide and tetrahydrofuran. This is a very clean reaction to the compounds 19a and 19b in tetrahydrofuran and the reaction will not proceed past this point to give either compound 1 or 2.

Treatment of either 18a or 18b with potassium tertiary butoxide and dimethylsulfoxide, on the other hand, gives the cycloalkylmethylnorthebaine derivatives 1 and 2, respectively. These compounds can also be obtained from compounds 19a and 19b by treatment with potassium tertiary butoxide and dimethylsulfoxide.

The compounds 1 and 2, as mentioned earlier, are valuable intermediates for production by total synthesis of the agonist-antagonis and the narcotic antagonist drugs Buprenorphine, Nalbuphine, Naltrexone, Nalmefene and other related compounds based on the thebaine type C-ring present in 1 and 2.

As an alternate route to 17a and 17b, bromoamides 14a and 14b can be debrominated to 20a and 20b by hydrogenation with palladium/carbon in methanol. The 20a and 20b produced by this reaction can then be converted to 17a and 17b using the same series of reactions shown in Chart 1 for transformation of the corresponding bromo derivatives 14a and 14b to 17a and 17b.

In the description of the total synthesis above there are certain steps which are major points in the present work:

(a) the unexpectedly successful Grewe cyclization of 12a and 12b, which occurs in the presence of super acids and inherently unstable small cycloalkyl rings, such as cyclopropyl and, to a lesser extent, cyclobutyl;

(b) the oxide bridge closure of 13a and 13b to 14a and 14b—this oxide bridge closure involves bromination of the 13a and 13b which generates hydrobromic acid. The cyclopropane ring present in 13a was found to be stable to the hydrobromic acid produced in the bromination and also, this oxide bridge closure occurs in neutral amide 13a in contrast to classical work in which the oxide bridge closure had been done within the basic N-nor series or in the N-methyl series.

(c) Compounds 14a and 14b, the bromoamides, can be hydrogenated in the presence of palladium in methanol to provide a quantitative yield of the corresponding desbromo derivatives 20a and 20b. In this hydrogenation reaction, the cyclopropane ring remains intact and ordinary prior art and teachings in elementary organic textbooks note that cyclopropane rings are unstable to catalytic hydrogenation, especially in the presence of palladium which tends to promote hydrogenolysis-type opening of small rings such as cyclopropane.

(d) Compounds 20a and 20b in the total synthesis are new by this particular process and they may be converted to 17a and 17b using an analogous series of reactions proceeding from 14a and 14b to 16a and 16b via 15a and 15b.

EXAMPLE 1

Synthesis of 13a from (+)-8.

A well-stirred mixture of 11.5 g (137 mmol) of $NaHCO_3$, 150 ml of $H_2O$, 150 ml of $CHCl_3$ and 20.0 g (66.4 mmol) of the (+)-isomer 8 was treated at 20°-25° C. dropwise with 8.29 g (79.7 mmol) of cyclopropylcarbonyl chloride in 30 ml of $CHCl_3$. After about 0.5 h, TLC indicated the absence of 8 and 10.0 ml of concentrated $NH_4OH$ was added. The $CHCl_3$ layer was separated and the aqueous phase was extracted with 2×50 ml of $CHCl_3$. The combined $CHCl_3$ extract was dried with $Na_2SO_4$, filtered and evaporated to give compound 9a as a foam. This crude 9a was dissolved in 445 ml of dry tetrahydrofuran containing 4.5 ml of $CH_3SO_3H$ and 8.26 g (133 mmol) of dry ethylene glycol. After standing 1.0 h at 25° C., conversion of 9a to ethylene ketal 10a was complete by TLC. The solution of 10a was treated at 0° C. with 9.16 g (66.4 mmol) of N-bromoacetamide in small portions during 0.5 h. After stirring an additional 0.5 h, the mixture was rendered alkaline with excess $NH_3$ gas, evaporated to a semisolid and the mixture was partitioned between 5 ml of concentrated $NH_4OH$, 300 ml of $H_2O$ and 100 ml of $CHCl_3$. The $CHCl_3$ was separated and the aqueous extracted with 2×75 ml of $CHCl_3$. The combined $CHCl_3$ was washed with 200 ml of $H_2O$ and evaporated to syrupy 11a which crystallized. A small portion was recrystallized from ethanol for analysis and showed mp 207.5°–209° C.

Analysis: Calcd for $C_{23}H_{28}BrNO_5$ (478.374); C, 57.74; H, 5.90; N, 2.93. Found C, 57.56; H, 6.13; N, 2.79. Chemical ionization ($NH_3$) mass spectrum $M+1^+ = 477/479$.

The bulk of the crude crystalline 11a was deketalized to 12a by dissolving in 75 ml of 88% $HCO_2H$ and allowing to stand at 25° C. for 30 min. The mixture was poured into 400 ml of $H_2O$, and extracted with 4×50 ml of $CHCl_3$. The combined $CHCl_3$ extracts were dried with $MgSO_4$ filtered and evaporated to give crude 12a which was dissolved in 30 ml of $CHCl_3$ and added slowly in 87 ml of dry $CF_3SO_3H$ with stirring and cooling to maintain a temperature of 15°–20° C. After stirring 20 h at 20°–25° C., the mixture was poured onto a stirred mixture of 115 ml of $CHCl_3$ and 252 g of ice. The $CHCl_3$ ws separated and the aqueous was extracted with 3×25 ml of $CHCl_3$. The combined $CHCl_3$ extracts were extracted with 3×100 ml of 1N NaOH. The $CHCl_3$ was then washed with 300 ml of $H_2O$ dried ($MgSO_4$) and evaporated to a solid. The solid was triturated with 50 ml of boiling isopropanol and the slurry concentrated to 35 ml, cooled to 20° C. and filtered to afford 13.76 g of morphinan 13a, mp 231.5°–233.5° C. Concentration of the filtrates and washings afforded a second and third crop of 1.35 g and 0.66 g, respectively (total yield=55%).

EXAMPLE 2

Oxide bridge closure of 13a to 14a.

A stirred solution of 6.01 g (13.84 mmol) of 13a in 100 ml of $CHCl_3$ was treated with 2.32 g of $Br_2$ (1.05 eq, 14.53 mmol) during 2 hr. The $Br_2$ was introduced as vapor entrained in a slow stream of argon gas. When the addition of $Br_2$ was complete, stirring was continued 15 min, then 50 ml of 1N NaOH was added and stirring was continued 0.5 h. The $CHCl_3$ was separated and the aqueous re-extracted with 10 ml $CHCl_3$. The combined $CHCl_3$ was evaporated to give 6.00 g of crude 14a, which showed mp 157.5°–159.5° C. after recrystallization from ethyl acetate.

EXAMPLE 3

Conversion of 14a to 17a.

A stirred mixture of 14a (864 mg, 2.0 mmol) 0.5 ml of methanol, 424 mg of trimethyl orthoformate (4.0 mmol), 152 mg of p-toluene-sulfonic acid.$H_2O$ and 3 ml of ethanol-free $CHCl_3$ was refluxed 1.0 hr to afford 15a containing traces of 16a. Conversion of 15a to 16a was completed by addition and distillation of 30 ml of ethanol free $CHCl_3$ in 10 mL portions. TLC showed the absence of 15a when distillation was complete. The mixture was treated with excess $NH_3$ gas, and partitioned between 1 ml concentrated $NH_4OH$, 20 ml $CHCl_3$ and 20 ml of $H_2O$. The $CHCl_3$ was separated, dried ($Na_2SO_4$) and evaporated to foamy 16a, which was refluxed in 20 ml toluene with 2.0 g of 70% (in benzene) $NaAlH_2(OCH_2CH_2—OCH_3)_2$ until TLC showed the absence of 16a and a transient intermediate spot corresponding to the 1-bromo derivative of 17a (about 5 h). The mixture was cooled, treated with 10 ml of 15% NaOH, and the toluene layer separated. The aqueous was extracted with 5 ml toluene, and the combined toluene extracts were dried ($Na_2SO_4$), evaporated and the residual 17a treated with 190 mg of anhydrous oxalic acid in 4 ml of acetone to give 836 mg (94%) crystalline 17a.$HCO_2CO_2H$. mp 199°–200° C. Alternately, the crude 17a could be crystallized from toluene-isooctane to afford 17a as the base, mp 113°–114° C.

EXAMPLE 4

Synthesis of N-cyclopropylcarbonylnorthebaine (1) from 17a.

A stirred solution of 577 mg (1.64 mmol) of base 17a in 10 ml of methanol containing 170 mg (1.05 eq) of $CH_3SO_3H$ was treated at 0° C. with 230 mg of 98% N-bromoacetamide (1.65 mmol) in small portions during 15 min. After stirring an additional 15 min (negative starch-iodide test) the mixture was rendered alkaline with $NH_3$ gas, evaporated and partitioned between $H_2O$ (20 ml) and $CHCl_3$ (20 ml). The $CHCl_3$ was separated, dried ($Na_2SO_4$), evaporated, and the residue was dissolved in 10 ml dry toluene and evaporated. The crude but essentially pure 18a was heated at 80° C. for 3.0 h in a mixture of 3 ml of dimethylsulfoxide containing 918 mg (5 eq) of potassium t-butoxide. The mixture was then cooled, diluted with 20 ml $H_2O$, and extracted with 3×15 ml of $Et_2O$. The ether was dried ($Na_2SO_4$), evaporated and the residual 1 was treated with 226 mg (1.64 mmol) of salicylic acid in 5 ml isopropanol to give crystalline material almost immediately. The solid was filtered, washed with isopropanol, and dried in vacuo to give 601 mg N-cyclopropylmethylnorthebaine salicylate (1 salicylate) mp 197°–198° C.

EXAMPLE 5

Alternate conversion of 14a to 17a.

The crude 14a from Example 2 was dissolved in 50 ml of MeOH containing 3.84 g of NaOAc.$3H_2O$ and 600 mg of 10% Pd/C. The mixture was hydrogenated 1.5 h at 50 psi $H_2$, filtered through celite, and the filter washed with MeOH. The filtrate and washings were evaporated, treated with 60 ml $H_2O$ and the mixture was extracted with $CHCl_3$ (60 ml, 10 ml). The combined $CHCl_3$ was extracted with 25 ml 15% NaOH, dried ($MgSO_4$) and evaporated to give 4.81 g (99%) of crude, crystalline 20a. A small portion was recrystallized from isopropanol and showed mp 141.5°–143° C. The bulk of the crude material was refluxed 1 h with 2.94 g (27.68 mmol) of (CH₃O)₃CH, 1.06 g (5.53 mmol) of p-toluene sulfonic acid, 3.5 ml MeOH and 21 ml of ethanol-free CHCl₃ to give the corresponding desbromo derivative of 15a. Addition and distillation of 3×40 ml of ethanol free CHCl₃ gave complete conversion to the corresponding desbromo derivative of 16a. The mixture was treated with excess NH₃ gas, then 25 ml of 1N NaOH and the CHCl₃ was separated. The aqueous was extracted with 20 ml CHCl₃ and the combined CHCl₃ was evaporated to give the desbromo derivative of 16a. This material was dissolved in 50 ml of dry toluene, evaporated, redissolved in 25 ml dry toluene and added to a refluxing solution of 8.4 g of 70% (in benzene) NaAlH₂(OCH₂CH₂OCH₃)₂. After 0.5 h of reflux, the mixture was cooled, treated cautiously with 20 ml of 15% NaOH. The toluene was separated, washed with 25 ml H₂O, dried (Na₂SO₄) and evaporated. The residue was dissolved in 10 ml acetone, treated with 1.26 g anhydrous oxalic acid in 8 ml acetone to give 4.86 g (79% from 14a) of 17a.HCO₂CO₂H, mp 195°–196° C., which showed several trace impurities.

EXAMPLE 6

In an analogous manner, to the above examples 1–5, (+)-8 was treated with cyclobutylcarbonyl chloride to give 9b which was converted to 13b mp 219°–223° C. as described above through 10b, 11b, and 12b. Transformation of 13b to 2, mp 102°–4° C., was accomplished through intermediates 14b, 15b, 16b, 17b, 18b and 19b. Conversion of 14b to 17b using a series of reactions analogous to those shown in example 5 for conversion of 14a to 17a is also possible.

Where the terms hydrocarbon and halogenated hydrocarbon are utilized in the specification and claims, the preferred hydrocarbons are benzene hydrocarbons which include toluene and xylene, and the preferred halogenated hydrocarbons are lower aliphatic halogenated hydrocarbons which include such solvents as chloroform, ethylene dichloride, methylene chloride and trichloroethylene. The term "Super acid" or "super acids" is defined to mean and include in this specification and claims the following: All protic acids stronger than 100% sulfuric, thus in this group are perchloric acid HClO₄, fluorosulfuric HSO₃F, the trifluoromethane sulfonic acid CF₃SO₃H, as well as trifluoroethane sulfonic acid. See review in *Science*, 26(4414): 13–20, Oct. 5, 1979.

I claim:

1. An improved total synthesis for the production of morphinan compounds which comprises heating a mixture of an amine compound of formula 3

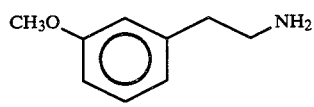

and pure acid compound 4

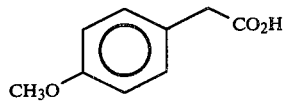

at 200° C. for about two hours under argon or other inert gas to obtain an amide, compound 5

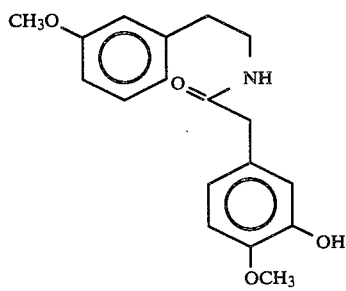

contacting compound 5 with phosphorus oxychloride to produce the 1,2-dehydro derivative, compound

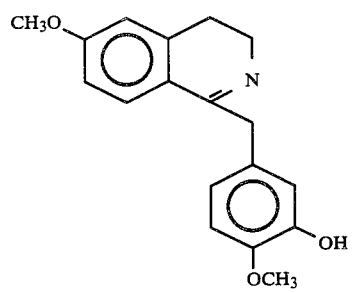

which need not be isolated;

neutralizing a solution of the crude 1,2-dehydro derivative 6 with aqueous ammonia and reducing with sodium borohydride or sodium cyanoborohydride to give tetrahydroisoquinoline, compound 7

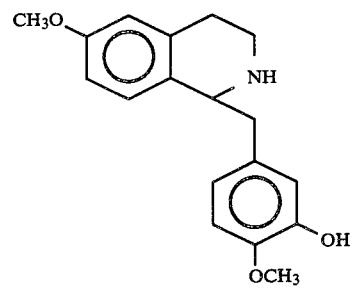

optical resolution of tetrahydroisoquinoline, 7, with tartaric acids or nitrotartranilic acids gives compound (+)-7, or alternately asymmetric reduction of 6 with chiral hydride reagents gives compound (+)-7

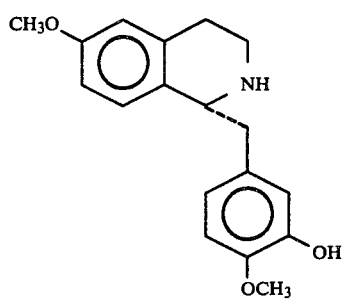

(+)-7 treating compound (+)-7 in liquid NH3 or lower alkyl amine with lithium and a mixture of tetrahydrofuran and t-butanol containing potassium tertiary butoxide to give the Birch base compound (+)-8

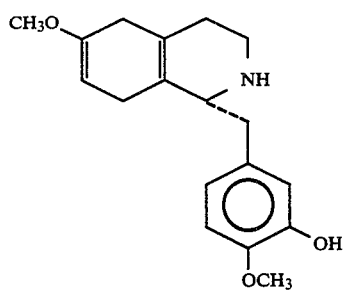

(+)-8 treating compound (+)-8 with cyclopropylcarbonyl chloride in a two-phase mixture of aqueous carbonate and hydrocarbon or halogenated hydrocarbon to give compound 9a, where R=cyclopropylcarbonyl

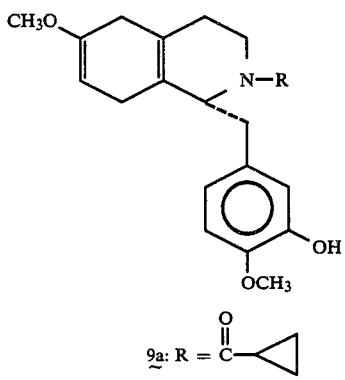

9a: R = C(=O)-cyclopropyl analogously treating compound (+)-8 with cyclobutylcarbonyl chloride in the same two-phase systems to give the corresponding compound 9b

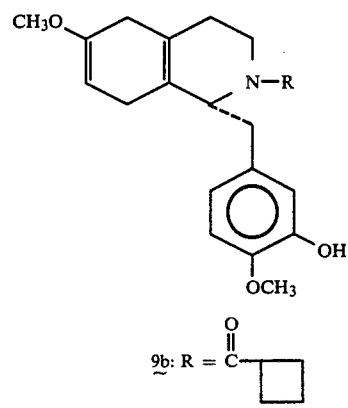

9b: R = C(=O)-cyclobutyl treating 9a and 9b separately with ethylene glycol and an acid catalyst in tetrahydrofuran to give compounds 10a and 10b, respectively, which need not be isolated

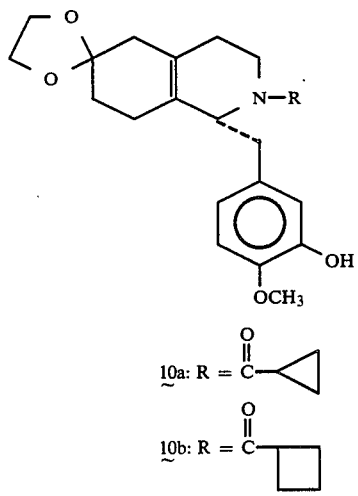

10a: R = C(=O)-cyclopropyl

10b: R = C(=O)-cyclobutyl directly brominating compounds 10a and 10b separately with N-bromo acetamide to give the corresponding bromoethylene ketals 11a and 11b, respectively

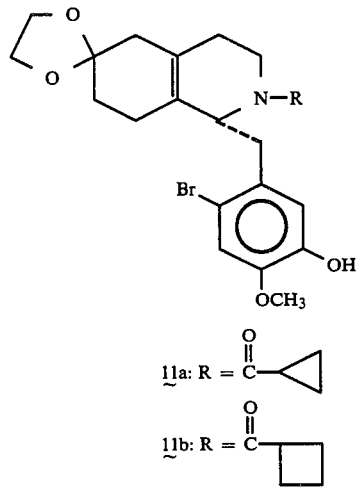

11a: R = C(=O)-cyclopropyl

11b: R = C(=O)-cyclobutyl deketalizing bromoethylene ketals 11a and 11b separately by a treatment with 88% formic acid to give compounds 12a and 12b, respectively

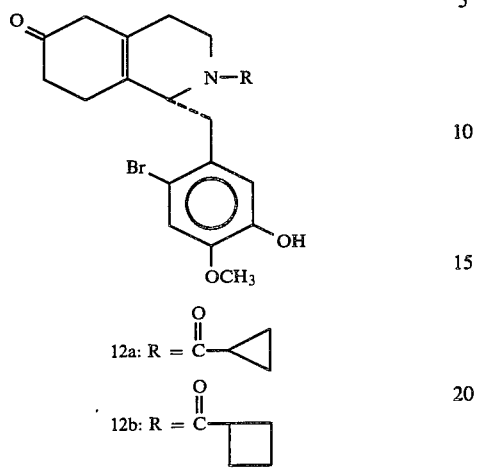

12a: R = $\overset{O}{\underset{\|}{C}}$—△

12b: R = $\overset{O}{\underset{\|}{C}}$—□ treating compounds 12a and 12b separately with a super acid to give compounds 13a and 13b

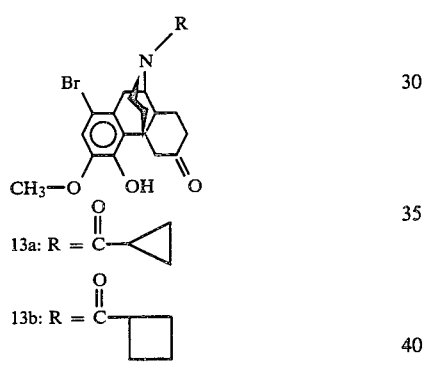

13a: R = $\overset{O}{\underset{\|}{C}}$—△

13b: R = $\overset{O}{\underset{\|}{C}}$—□ treating compounds 13a and 13b separately with about an equal molar amount of bromine in hydrocarbon, halogenated hydrocarbon or acetic acid followed by treating with excess sodium hydroxide to give compounds 14a and 14b, respectively

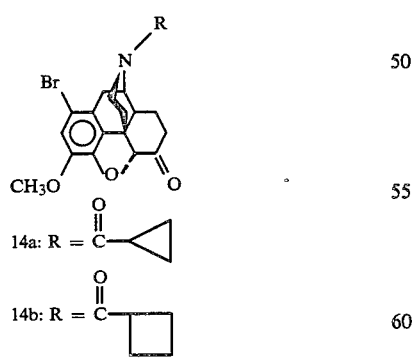

14a: R = $\overset{O}{\underset{\|}{C}}$—△

14b: R = $\overset{O}{\underset{\|}{C}}$—□ treating compounds 14a and 14b separately with trimethylorthoformate, methanol, a sulfonic acid and a benzene hydrocarbon or halogenated lower aliphatic hydrocarbon solvent to give compounds 15a and 15b, respectively, which need not be isolated

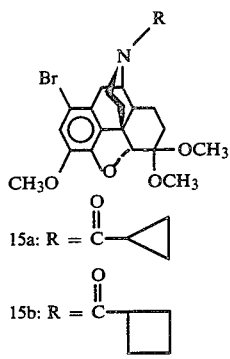

15a: R = $\overset{O}{\underset{\|}{C}}$—△

15b: R = $\overset{O}{\underset{\|}{C}}$—□ converting compounds 15a and 15b separately by distillation of the hydrocarbon or halogenated hydrocarbon solvent to the corresponding enolether 16a and 16b, respectively

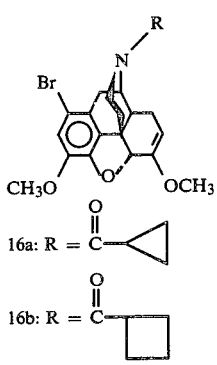

16a: R = $\overset{O}{\underset{\|}{C}}$—△

16b: R = $\overset{O}{\underset{\|}{C}}$—□ reducing the bromoamides 16a and 16b separately with a complex metal hydride selected from one member of a group consisting of LiAlH₄ or NaAlH₂(OCH₂CH₂—OCH₃)₂ to give the corresponding amine compounds 17a and 17b, respectively, where R=cyclopropylmethyl and cyclobutylmethyl, respectively

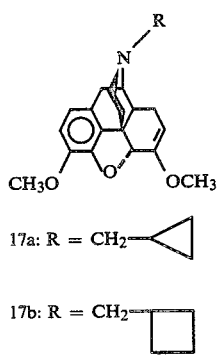

17a: R = CH₂—△

17b: R = CH₂—□ treating 17a and 17b separately with N-bromo acetamide in methanol to give compounds 18a and 18b, respectively thylnorthebaine derivatives, compounds 1 and 2, respectively

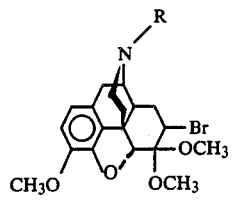

18a: R = CH₂—◁

18b: R = CH₂—□ treating 18a and 18b separately with potassium tertiary butoxide and tetrahydrofuran to give the corresponding cycloalkylmethyl norcodeinone dimethylketal compounds 19a and 19b, respectively

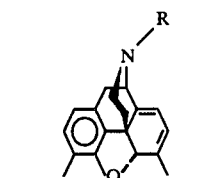

1: R = CH₂—◁

2: R = CH₂—□ hydrogenating the bromoamides 14a and 14b separately in the presence of palladium/carbon in methanol to provide a near quantitative yield of the corresponding desbromo derivatives, compounds 20a and 20b

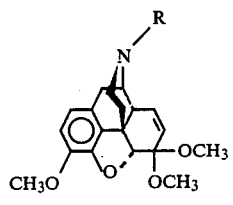

19a: R = CH₂—◁

19b: R = CH₂—□ treating 19a and 19b separately, or alternately 18a and 18b separately, with potassium tertiary butoxide and dimethylsulfoxide to give the cycloalkylme-

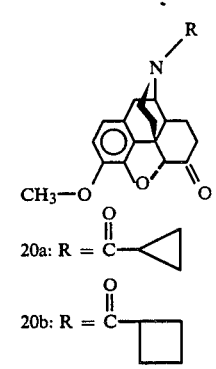

20a: R = $\overset{O}{\underset{\|}{C}}$—◁

20b: R = $\overset{O}{\underset{\|}{C}}$—□ converting 20a and 20b separately to compounds 17a and 17b, respectively, by an analogous series of reactions proceeding from 14 to 15 to 16.

* * * * *